United States Patent [19]
Augurt

[11] Patent Number: 5,200,147
[45] Date of Patent: Apr. 6, 1993

[54] COMPACT PREVACUUM STEAM STERILIZER TEST PACK

[75] Inventor: Thomas A. Augurt, New Canaan, Conn.

[73] Assignee: Propper Manufacturing Co., Inc., Long Island City, N.Y.

[21] Appl. No.: 823,089

[22] Filed: Jan. 15, 1992

Related U.S. Application Data

[63] Continuation of Ser. No. 489,204, Mar. 5, 1990, abandoned.

[51] Int. Cl.$^5$ .......................................... G01N 31/22
[52] U.S. Cl. ........................................ 422/56; 422/58; 422/61; 422/87; 436/1
[58] Field of Search ................................. 422/56-58, 422/61, 87; 436/1

[56] References Cited

U.S. PATENT DOCUMENTS

| | | | |
|---|---|---|---|
| 4,486,387 | 12/1984 | Augurt | 422/58 |
| 4,576,795 | 3/1986 | Bruso | 436/1 |
| 4,579,715 | 4/1986 | Bruso | 436/1 |
| 4,596,696 | 6/1986 | Scoville, Jr. | 422/61 |
| 4,692,307 | 9/1987 | Bruso | 422/58 |

Primary Examiner—Jill A. Johnston
Attorney, Agent, or Firm—Amster, Rothstein & Ebenstein

[57] ABSTRACT

A prevacuum steam sterilization test pack, for testing the efficiency of the vacuum system of a steam sterilizer apparatus to create a vacuum, comprises a bundle of layers and a porous overwrap folded about the bundle to maintain the integrity thereof. The bundle includes a porous test sheet with a steam sensitive indicator ink printed thereon positioned between layers of the bundle to indicate the efficiency of the vacuum system of a sterilizer, a plurality of selectively porous layers within the bundle above and below said test sheet, and at least one pair of non-porous gas-impermeable layers disposed intermediate the test sheet and one of the bundle end surfaces. The pair of non-porous layers is spaced from both the test sheet and the one bundle end surface by at least one of the porous layers, and the non-porous layers are spaced apart by at least one and no more than two of the porous layers. The number, the position and spacing apart of the non-porous layers depend upon a predesignated degree of efficiency.

12 Claims, 2 Drawing Sheets

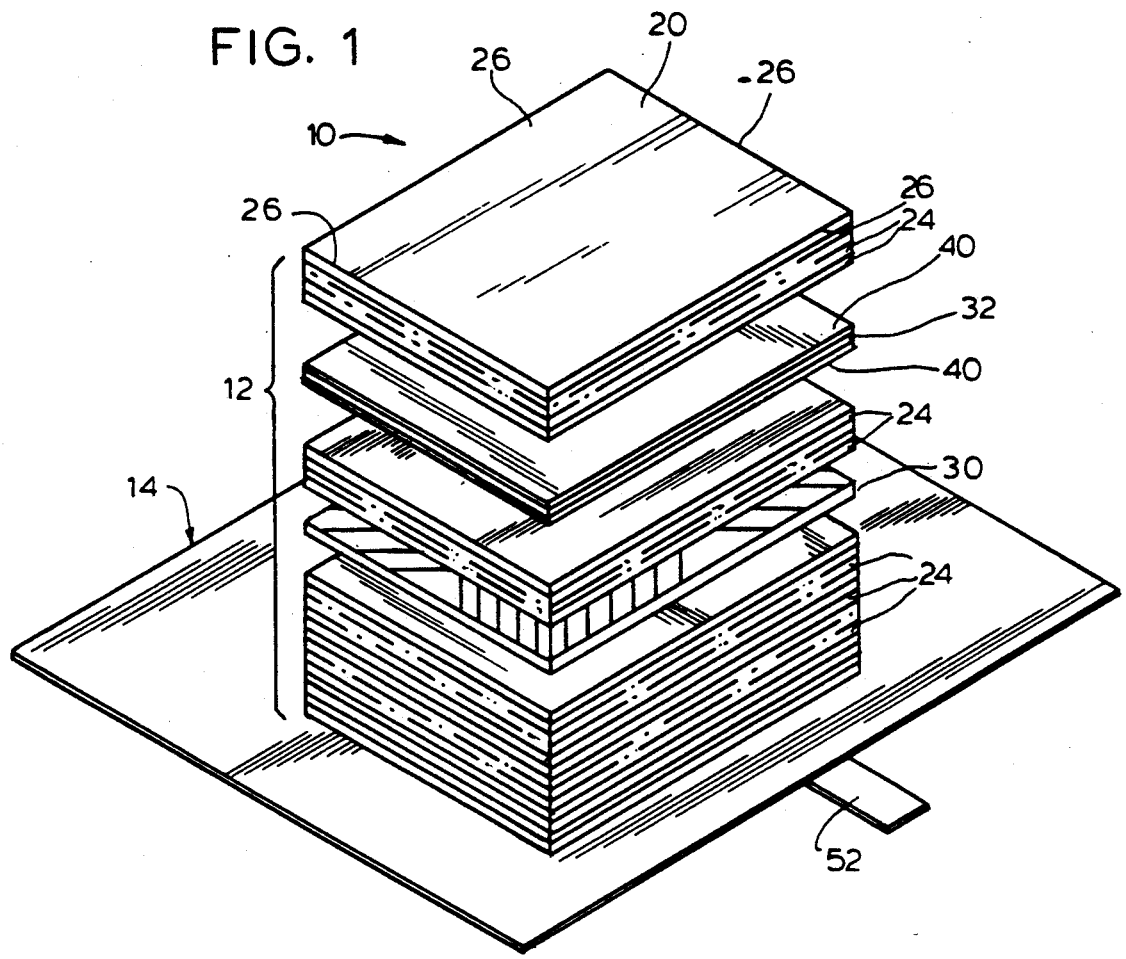
FIG. 1
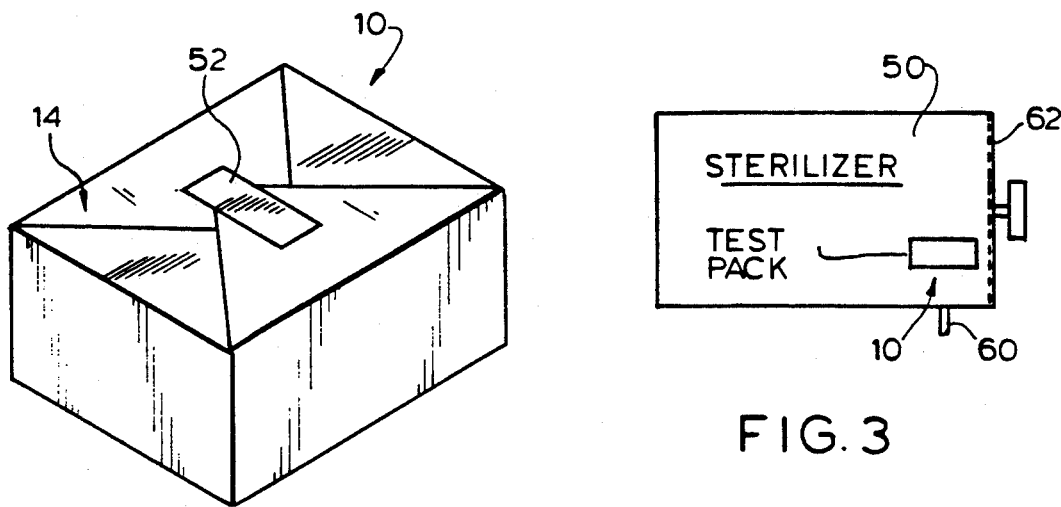
FIG. 2
FIG. 3

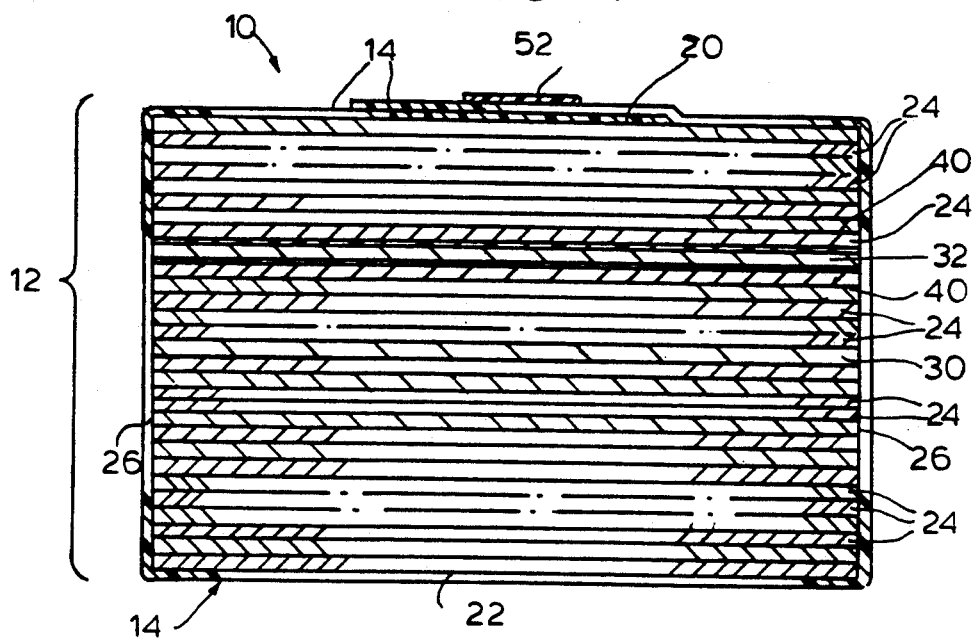

COMPACT PREVACUUM STEAM STERILIZER TEST PACK

This is a continuation of application Ser. No. 07/489,204 filed on Mar. 5, 1990 and now abandoned.

BACKGROUND OF THE INVENTION

This invention relates generally to the sterilization of medical and surgical products, and more specifically to a test pack adapted to be processed through a conventional sterilization cycle in a prevacuum steam sterilizer to check the proper operation of the sterilizer.

In the sterilization of medical dressings and instruments by steam, such dressings or instruments are conventionally assembled in bundles or packs and placed in a steam sterilization chamber which is sequenced through an appropriate sterilization cycle. Individual packages may contain stacks of towels, dressings, sponges and similar materials or may contain desired complements of surgical instruments or equipment for specific surgical procedures.

A current method of steam sterilization practice involves the placement of such packs in a sterilizer, the evacuation of air from the sterilizer and the introduction of saturated steam at a desired pressure to produce a desired temperature (typically 270°-276° F.) for a selected period of time. Prevacuum sterilizers operating in this manner have frequently replaced the downward displacement or gravity air discharge sterilizers previously used. The significant advantage of the prevacuum method is that removal of air before introduction of steam permits the rapid penetration of steam throughout the surgical pack. Elimination of air is necessary in all steam sterilizers since air trapped in the packages would prevent sterilization of the portion of the pack's interior where it collected. With the prevacuum method, the time required for steam penetration in a typical sterilization cycle is greatly reduced, and prevacuum sterilizers currently operate on a relative short cycle (with an exposure time on the order of 4 minutes at 134° C.). The operation of such sterilizers is well described in John J. Perkins, *Principles and Methods of Sterilization, in the Health Sciences,* published by Charles C Thomas, Springfield, Illinois. Chapter VI, "Prevacuum High Temperature Sterilization."

The ability to sterilize instruments in a shortened time, however, is dependent on the assumption that air is properly evacuated from the sterilizer. This includes the expectation that the vacuum system is functioning properly to evacuate the chamber initially and that there are no air leaks in the sterilizer or the vacuum lines which would permit introduction of air after the vacuum is drawn. During routine use, wear on certain sterilizer parts will eventually result in air leaks, and there is a need to test the sterilizer on a periodic (daily) basis to ascertain whether the vacuum system is functioning properly.

In 1961, a test procedure was proposed by J. Dick et al. and described by J.H. Bowie, et al. of the Department of Microbiology, Royal Infirmary, Edinburgh, Scotland in an article appearing in The Lancet, Mar. 16, 1963, pp. 586-587, which suggested a protocol for determining that the sterilizer was in proper working order, and that the vacuum system was operating properly. As indicated in the article, residual air in the system at the time steam is introduced will be swept by the steam pressure into the pack, usually to the pack center. Trapped air in the pack inhibits proper steam penetration.

According to the Bowie and Dick protocol, autoclave tape was used in combination with a stack of surgical towels to test the working order of the sterilizer on a daily basis. Autoclave tape is an adhesive tape having printed on its top surface stripes of a chemical composition which has the property of changing color, for example from white to black, upon exposure to steam at an appropriate temperature for an appropriate period of time. According to the Bowie and Dick protocol, such tape was placed on a fabric sheet in a cross configuration, and the fabric sheet was then placed within a stack of folded surgical towels. The entire assembly was placed within the sterilizer. The sterilizer was run through its usual cycle with an exposure time of three and one-half minutes at 133°-134° C., after which the tape cross was examined to determine whether steam had completely penetrated the towel stacks effectively. A uniform color change was indication of a pass, and the presence of incompletely changed indicator color was a failure.

This protocol is currently in widespread use and is described in the *Association For The Advancement Of Medical Instrumentation (AAMI) Recommended Practice: Good Hospital Practice for Steam Sterilization and Sterility Assurance,* 1988 ed., published by the AAMI, 1901 North Ft. Myer Drive, Suite 602, Arlington, VA 22209. As indicated in Paragraph 6.7 of that publication, entitled "Prevacuum Sterilizer Residual Air Test," the test involves the use of 100% cotton huckaback towels, freshly laundered but not ironed (in view of the fact that excess dryness may affect the test results) folded in a 9"×12" configuration and piled 10"-11" high. The details of the Bowie and Dick procedure are described in the above-referenced *Recommended Practice.* Standards for sterilizer performance in other parts of the world may require different pack constructions to test for the desired sterilizer efficiency. For example, test packs which would provide an acceptable challenge in the U.S.A. would be considered to be inadequate in Europe, whereas a test pack considered to be adequate in Europe would overchallenge U.S. sterilizers.

The testing of prevacuum sterilizers according to the Bowie and Dick protocol involves a number of important shortcomings. Firstly, the test is subject to individual execution by the sterilization section of the hospital on a daily basis, and the various requirements of the Bowie and Dick Protocol—namely the type of towels or other fabrics used, their condition, age and the like (all of which affect the significance of the test result-)—may vary widely from day to day and from institution to institution. Secondly, the performance of the Bowie and Dick protocol is relatively inconvenient and costly in that the expense of laundering towels (which cannot be thereafter used without relaundering), assembling the test arrangement and the like involve costly hospital labor. Additionally, certain hospitals have elected to eliminate laundry facilities entirely, utilizing only single-use disposable fabrics for their procedures, making the proper conduct of the Bowie and Dick protocol more inconvenient.

Attempts have been made to permit the use of a test sheet without the use of the conventional stacks of cotton towels in accordance with the Bowie and Dick protocol. As indicated in the literature on the Bowie and Dick protocol, various types of defects are most frequently found in sterilization equipment. Principal among these are (1) inadequacy of initial vacuum, leaving residual air within the packs, and (2) air leaks within the chamber or vacuum system which permit the re-entrainment of air after a vacuum has been drawn. In designing a test pack to evaluate both these types of flaws, as well as others, it was discovered that there are a variety of different constraints operating.

For example, to the extent a flaw is present in the vacuum system which prevents a sufficient vacuum from being formed in the first instance, a test pack having a low porosity and/or high bulk is more likely to reveal a flaw of this type than one having a high porosity and/or lower bulk. As the vacuum is drawn, the air within the test pack tends to be drawn out of the pack. Low porosity and/or very bulky material surrounding the test sheet would tend to increase the difficulty of removal of such air and increase the likelihood that the test pack would indicate a flaw.

On the other hand, flaws caused by leaks involve the introduction of air into the sterilizer after the vacuum has been drawn. In this situation, the relationship between the porosity of the material surrounding the test sheet and sensitivity of the test is the reverse. The less porous and/or more bulky the material surrounding the test sheet, the less likely it is that air introduced into the sterilizer after the vacuum has been drawn (as in the case of a leak) will re-enter the test pack. Accordingly, with respect to a flaw resulting from air leaks after a sufficient vacuum has been drawn, low porosity material surrounding the test sheet would tend to make it more difficult for air from such a leak to enter the pack and decrease the likelihood that such a test pack would indicate a flaw.

In order to properly test the sterilizer, a test pack must provide an appropriate, but not excessive challenge to the vacuum system using as a guideline the challenge provided by the currently accepted towel pack standard for the Bowie and Dick protocol. It is desirable to design a relatively small, inexpensive and disposable test pack which achieves a challenge to the sterilizer comparable to the challenge provided by the accepted Bowie and Dick protocol.

Exemplary of the various attempts to provide a Bowie and Dick-type test pack without using towels are the multilayer test packs described in U.S. Pat. Nos. 4,486,387; 4,576,795; 4,579,715; 4,596,696; and 4,692,307. For example, according to U.S. Pat. No. 4,486,387, a multilayer disposable test pack is composed of a sterilization test sheet having defined areas adapted to change color in response to the presence of steam under selected exposure conditions, surrounded by a set of disposable non-woven porous sheets of material arranged in overlying relation above and below the test sheet. The innermost sheets of material form an inner core region around the test sheet, and the remaining sheets form an outer shell region, with the porosity and bulk of the inner core region and the porosity of the outer shell region being selected so as to define a desirable challenge to the sterilizer.

The test pack of U.S. Pat. No. 4,486,387 is designed to be used according to the accepted Bowie and Dick protocol and to be placed in an otherwise empty sterilization chamber, sequenced through a predetermined cycle and removed. The pack is then opened and the interior test sheet examined for evidence of inadequate steam penetration, air bubbles and like defects. The presence of such defects indicates faults in the vacuum or other systems within the sterilization unit which require evaluation and repair. The test is intended to be performed on a daily basis with the interior test sheet forming a permanent record of such testing. The non-woven sheet material and the remainder of the pack are disposed of after a single use.

Such a test pack provides detection of the common sterilizer flaws in a manner comparable to the Bowie and Dick Protocol. Nonetheless, these multilayer test packs have not been found to be entirely satisfactory. Their complex construction requires a large number of sheets to be arranged in appropriate sequence and number and then packaged with overwrap or placed in an outside container providing a predetermined tightness. The complexity of the construction and the care required in assembling the same adds to the cost of the product. While the conventional multilayer test packs are generally about $5 \times 5 \times \frac{1}{4}$ inches in the U.S. and about $5 \times 4 \times 1$ inches in Europe, and thus substantially smaller than the towel packs required by the Bowie and Dick protocol, they are still relatively bulky when stored in quantity for daily tests. Accordingly, the need remains for a test pack which is composed of fewer sheets, thereby reducing the complexity of the construction and the care required in assembling the same, and thus the overall costs of the product. Further, the need remains for a test pack which is somewhat smaller than the presently available test packs, so that they present less bulk when stored in quantity for daily tests.

While some of the conventional multilayer test packs utilize a non-porous sheet of reduced steam and/or air permeability in order to enable a reduction of the overall size of the test pack without compromising the challenge presented to the stabilizer, the addition of the non-porous layer reduces the porosity of the test pack considerably and typically only one such sheet is used to either side of the test sheet (that is, one non-porous sheet intermediate the test sheet and each bundle end surface). It is in conventional thinking that the effect of a non-porous sheet is so strong that only one such non-porous sheet should be used between the test sheet and a bundle end surface or, if more than one is used, each non-porous sheet should be separated by numerous porous sheets.

Accordingly, it is an object of the present invention to provide a relatively small, inexpensive and disposable test pack for use in prevacuum steam sterilizers to determine whether the sterilizer is functioning in accordance with proper standards by simulating air evacuation and steam penetration conditions of the conventional pack described in the Bowie and Dick protocol so as to define an appropriate challenge for a residual air test in a prevacuum sterilizer.

Another object is to provide such a test pack for prevacuum sterilizers which provides a repeatable and consistent standard for testing the working order of the sterilizer from day to day and from sterilizer to sterilizer, yet requires neither assembly by hospital personnel nor the use of hospital linen or laundries for its initial use.

A further object is to provide such a test pack utilizing fewer layers than other comparable multilayer test packs.

A still further object is to provide such a test pack which is more compact than a conventional multilayer test pack offering a similar challenge in at least one and preferably two or even three dimensions.

SUMMARY OF THE INVENTION

It has now been found that the above and related objects of the present invention are obtained in a compact prevacuum steam sterilization test pack for testing the efficiency of the vacuum system of a steam sterilizer apparatus to create a vacuum. The test pack comprises a bundle of layers and a porous overwrap folded about the bundle to maintain the integrity thereof. The bundle has a pair of end surfaces including a top surface and a bottom surface, a plurality of layers therebetween, and an edge between the top surface and the bottom surface. More specifically, the bundle includes a porous test sheet with a steam sensitive indicator ink printed thereon positioned between layers of the bundle to indicate the efficiency of the vacuum system of a sterilizer. The bundle also includes a plurality of selectively porous layers within the bundle above and below the test sheet. The bundle further includes at least one pair of non-porous gas-impermeable layers disposed intermediate the test sheet and one of the end surfaces and spaced from both the test sheet and the one end surface by at least one of the porous layers. The non-porous layers of the pair of non-porous layers are spaced apart by at least one and no more than two of the porous layers, the number, the position and spacing apart of the non-porous layers depending upon a predesignated degree of efficiency.

In a preferred embodiment, the pair of non-porous layers is closer to the test sheet than to the one end surface and is spaced from the one end surface by a greater number of porous layers than it is from the test sheet. The non-porous layers of the pair of non-porous layers are spaced apart by substantially no more than one of the porous layers, with the non-porous layers of the pair of non-porous layers optimally being disposed on (e.g., laminated to) opposed surfaces of the one porous layer. The bundle includes a plurality of the pairs of the non-porous layers, at least one of the pairs of non-porous layers being disposed to each side of the test sheet. The bundle may include a triplet of non-porous layers disposed to each side of the test sheet, with each non-porous layer of the triplet being spaced apart from an adjacent non-porous layer of the triplet by at least one and no more than two of the porous layers.

The non-porous layers are gas-impermeable plastic, and each of the non-porous layers is thinner than one of the porous layers. Nonetheless, the pair of non-porous layers restricts the escape of gas from the bundle therethrough when steam enters the bundle during operation of a sterilizer and establishes the amount of exposure of the indicator ink on the test sheet to steam as an indication of the efficiency of the vacuum system of the sterilizer.

BRIEF DESCRIPTION OF THE DRAWING

Further objects, features and advantages of the present invention will be more fully appreciated by reference to the following detailed description of the presently preferred, albeit illustrative, embodiments of the present invention, when taken in conjunction with the appended drawing, wherein:

FIG. 1 is an exploded isometric view of a test pack according to the present invention;

FIG. 2 is an isometric view of the test pack;

FIG. 3 is a schematic side elevation view of the test pack in a sterilizer;

FIG. 4 is a sectional view of the test pack;

FIG. 5A is a schematic representation of a conventional bundle for use in a multilayer test pack adapted for use in the United States, while FIGS. 5B-D are schematic representations of the bundles of generally equivalent compact multilayer test packs according to the present invention; and FIG. 6A is a schematic representation of a conventional bundle for use in a multilayer test pack adapted for use in Europe, while FIGS. 6B-C are schematic representations of the bundles of generally equivalent compact multilayer test packs according to the present invention.

DETAILED DESCRIPTION OF THE PREFERRED EMBODIMENTS

A test pack according to the present invention provides detection of the common sterilization flaws in a manner comparable to the Bowie and Dick protocol by establishing a package of individual sheets of disposable material above and below an appropriate test sheet. Thus the test pack permits the use of a test sheet such as the Once-A-Day sheet (available from Propper Manufacturing Co., Inc.) without the use of the conventional stacks of cotton towels in accordance with the Bowie and Dick protocol.

Referring now to the drawing, and in particular to FIGS. 1-2 and 4 thereof, therein illustrated is a prevacuum steam sterilization test pack according to the present invention, generally designated by the reference numeral 10. The test pack 10, which is preferably disposable, is designed to test the efficiency of the vacuum system of a steam sterilizer apparatus to create a vacuum. In its basic aspects, the test pack 10 comprises a bundle generally designated 12, and a porous overwrap generally designated 14, such as a flexible sheet or a box about the bundle 12 to maintain the integrity thereof.

More particularly, the bundle 12 has a pair of end surfaces including a top surface 20 and a bottom surface 22, a plurality of non-woven layers 24 therebetween, and opposed edges 26 between the top surface 20 and bottom surface 22.

The bundle 12 includes a sterilization test sheet 30 of a type known in the art. This test sheet 30 is generally a rectangular sheet of relatively porous paper which has printed on its top surface a steam sensitive ink in a test pattern designed to cover a substantial portion of the sheet surface. An appropriate test sheet for this purpose is the Once-A-Day test sheet manufactured by Propper Manufacturing Co., Inc. of 36-04 Skillman Avenue, Long Island City, New York. This test is similar in nature to that shown in U.S. Pat. No. Des. 222,516.

The ink areas of this test sheet 30 are adapted to change color from white to black upon exposure to steam at a desired temperature for a desired period. The color change from white to black occurs over a period of time so that insufficiency of steam exposure may result in only partial development of the ink from white to black. This partial change may result in white or brown or similarly light areas, visible on the test sheet, and indicates an unacceptable level of vacuum system efficiency. Test sheets of this type are generally known in the art and have been used in place of the cross sterilization tape strips described in the initial Bowie and Dick test procedure.

The bundle 12 further includes a plurality of selectively porous layers 32 both above and below the test sheet 30. The porous sheets 32 are preferably of the same configuration as the test sheet 30, typically rectangular. A wide variety of porous sheets 32 may be used or, alternatively, all of the porous sheets may be identical (with the exception of the test sheet 30). Preferably, different porous sheets are used in the bundle 12 both above and below the test sheet 30, for example, a mix of heavy porous sheets and light porous sheets. For example, each heavy porous paper sheet may have an appropriate basis weight of 214 lbs. (per 3,000 square feet), an appropriate thickness of approximately 0.02 inch per sheet, and a Gurley porosity of approximately 12-35 sec. for 1 sq. in. area per sheet (20 oz. cylinder); and each light porous paper sheet may have an approximate basis weight of 178 lbs. (per 3,000 sq. ft.), an approximate thickness of approximately 0.02 inch per sheet, and a Frazier porosity of approximately 1.2-2.0 cu. ft./sq. ft./min. per sheet. However, clearly other porous papers may be used for the porous layers 32.

Frazier porosity is the measure of air permeability of sheet material as measured by the Frazier Differential Pressure Air Permeability Measuring Machine manufactured by Frazier Precision Instrument Company, Inc. of 210 Oakmont Avenue, Gaithersburg, Md. 02760. These measures of porosity are based on the differential pressure principle as measured by manometers. The porosity measure is given in cubic feet of air per square foot per minute at 0.5 inches of water pressure.

Another common measure of porosity of sheet material is the Gurley method which provides a measure of the time required for 100 ml. of air to pass through one square inch area of the specimen material at a given pressure. Obviously, the Frazier porosities given herein in cubic feet per square foot per minute could be expressed by other standards of measurement. The porosity of stacked porous materials of the type herein used is substantially linear so that, if an individual sheet of material has a Frazier porosity of 90 cu. ft./sq.ft./min., a stack of ten sheets of such material will have a porosity 1/10 of that of the individual sheet or 9 cu. ft./sq. ft./min.

According to the present invention, the bundle 12 additionally includes at least one pair of non-porous gas-impermeable layers 40 disposed intermediate the test sheet 30 and at least one (and preferably each) of the bundle end surface 20, 22. Each non-porous layer 40 is formed at least in part of a gas-impermeable film-forming polymeric material, such as polypropylene, nylon, polyester, polycarbonate or like material capable of resisting the heat and moisture characteristic of a steam sterilizer, and is preferably a plastic. The non-porous layer 40 may be self-contained (that is, constitute a self-supporting sheet by itself), but is preferably only a film laminated to the face of a porous sheet by means well known in the art, as shown. For example, a plastic film may be heat bonded to a porous layer as described hereinabove or laminated thereto using a suitable adhesive, such as an acrylic-based, silicone, rubber or like adhesive, to form a sheet have a porous layer 32 and a non-porous layer 40 on one surface thereof. The non-porous layers 40 are typically laminated to low porosity 214 basis paper for ease of handling during the assembly process, but could alternatively be laminated to high porosity 178 basis paper. The non-porous layer 40 by itself is preferably 1-3 mil (0.001-0.003 inch) in thickness as thinner sheets are hard to handle and thicker sheets pose too hard a challenge to the test pack. A preferred thickness is approximately 2.3 mil (0.0023 inch per sheet). When measured for Frazier or Gurley porosity, this material exhibits no porosity.

It is critical to the present invention that the pair of non-porous sheets 40 is spaced from both the test sheet 30 and the bundle end surfaces 20, 22 by at least one of the porous layers 32. Disposition of the pair of non-porous layers 40 directly adjacent the test sheet 30 provides too exacting a challenge for the test pack, while disposition of the pair of non-porous layers 40 directly against a bundle end surface 30, 32 positions the pair of non-porous layers 40 so remotely from the test sheet 30 that it has less significance and fails to contribute the desired effect to the test pack challenge. Preferably, the pair of non-porous layers 40 disposed intermediate the test sheet 30 and one of the bundle end surfaces 20, 22 is disposed closer to the test sheet 30 than to the bundle end surface 20, 22 and is spaced from the bundle end surface by a greater number of porous layers 32 than it is from the test sheet 30. The closer the non-porous layers 40 are to the test sheet 30 and the fewer the number of porous layers 32 separating it from the test sheet 30, the greater the effect of the pair of non-porous layers 40 and the more severe the challenge posed by the test pack 10.

It is also critical to the present invention that the non-porous layers 40 of the pair of non-porous layers 40 are spaced apart by at least one and no more than two of the porous layers 32 (ignoring for the purpose of this rule any empty spaces between sheets). If the non-porous layers 40 of the pair are in direct contact (that is, not spaced apart by at least one of the porous layers 32), too exacting a challenge is provided, and, if the non-porous layers 40 of the pair are separated by more than two of the porous layers 32, the non-porous layers 40 fail to contribute the desired effect. Preferably, the non-porous layers 40 of the pair of non-porous layers are spaced apart by substantially no more than one of the porous layers 32. The less spaced apart the non-porous layers 40, the more significant their effect and the more severe the challenge presented by the test pack 10, all other factors being equal. It is especially preferred that the non-porous layers 40 of the pair are disposed on opposed surfaces of one porous layer 32—e.g., that there be a laminate composed of a porous layer 32 sandwiched between a pair of non-porous layers 40.

Preferably, the bundle 12 includes a plurality of the above-described pairs of non-porous layers 40. As the bundle 12 is typically symmetrical relative to the plane of test sheet 30, preferably there is at least one of the pairs of non-porous layers 40 disposed to each side of the test sheet 30. For a more severe challenge, at least a plurality of pairs of non-porous layers 40 are disposed to each side of the test sheet 30, intermediate the test sheet 30 and one of the bundle end surfaces 20, 22. Clearly, the greater the number of pairs of non-porous layers 40 disposed in a bundle 12, and in particular intermediate a test sheet 30 and each bundle end surface 20, 22, the more severe the challenge posed by the test pack 10.

Thus it must be appreciated that the number, the position and the spacing apart of the non-porous layers 40 affects the challenge presented and will depend upon the predesignated degree of efficiency which the test pack is designed to use as a dividing line between a pass or failure of the challenge.

The overwrap 14 is preferably a conventional CSR (central supply room) overwrap sheet, which may be held in place by conventional autoclave indicator tape 52 to maintain the components of the bundle 12 in the desired relationship. To form the test pack 10, the bundle 12 is assembled, either separately from the overwrap sheet or on top of an extended overwrap sheet, and the overwrap sheet is then wrapped around bundle 12 in the conventional manner and secured by the autoclave indicator tape 52. Alternatively the overwrap 14 may be a box constructed from an appropriate density solid, bleached sulfate board, into which the assembled bundle 12 is placed through an open end and the box then closed.

Referring now to FIG. 3, the test pack 10 is used by placing it in a conventional manner, on one of its end surfaces (parallel to a bundle end surface 20, 22), on a ledge (not shown) over the drain 60 of an empty sterilizer 50, adjacent the sterilizer door 62. The test pack 10, comprising the overwrap 14 and the bundle 12, may itself be placed in an overpackage or outer wrapping prior to insertion into the sterilizer 50. It will be appreciated that the test pack 10 of the present invention may be used to test any type of prevacuum steam sterilizer, including the high vacuum and pulse type prevacuum steam sterilizers.

Although each of the non-porous layers 40 is thinner than a porous layer 32, the pair of non-porous layers 40 restricts the escape of gas from the bundle therethrough when steam enters the bundle during operation of a sterilizer and establishes the amount of exposure of the indicator ink on the test sheet 30 to steam as an indication of the efficiency of the vacuum system of the sterilizer. The pair of non-porous layers 40 exert this significant effect even though they are much thinner (typically about 2 mil. or 0.002 in.) relative to the porous sheets (typically about 20 mil. or 0.02 in.).

Because the pairs of non-porous layers 40 provide a challenge to the passage of non-condensable gas and steam which is equivalent to that provided by a series of many porous layers 32 (whether more or less porous), the total number of layers 24 in a bundle 12 according to the present invention can be reduced to provide a test pack 10 of lesser height than a conventional multilayer test pack. Thus, the height of a test pack 10 according to the present invention may be reduced from about the ⅝ or 1 inch of a conventional multilayer test pack for the U.S. or Europe to about 9/16 or ⅜ inch, respectively, while still providing an equivalent challenge. The bundle 12 may also have smaller dimensions in the plane of the layers 24 the present invention may have layer dimensions of about 4×4 in., substantially less than the 5×5 in. or 5½×5½ in. or even larger multilayer test packs currently in use in the U.S. and abroad, while providing an equivalent challenge.

As indicated previously, it is desirable that the disposable test pack 10 respond to faults in the sterilizing equipment in a manner comparable to cotton towels prepared in accordance with the Bowie and Dick protocol. The preferred embodiments of the present invention accomplish this desired objective. Specifically, tests have been conducted in a specially modified prevacuum steam sterilizer altered to create conditions equivalent to sterilizer defects in a controlled and reproducible manner. The prevacuum steam sterilizer included a manually controlled vacuum pump permitting alteration in the degree of vacuum drawn in the system, and an adjustable-volume piston-driven air injector. Incomplete air removal was simulated by interrupting the pre-vacuum sequence of the sterilizer. Air leaks were created in a predictable and reproducible way by a manually set, micrometer-equipped needle valve. The results were evaluated by comparing the color changes shown on test sheets obtained with the pack described herein and standard towel packs as well as other commercially available pre-assembled packs proven to be equivalent to the standard towel pack.

The test sheet 30 is intended normally to be evaluated visually in the normal manner for such devices employed in the Bowie and Dick protocol. For the purpose of quantifying testing color changes in the chemical indicator sheet were evaluated by a reflectometer with a 10 millimeter orifice setting (Model XL-20 Gardener/Neotec Instrument Division of Pacific Scientific, Silver Spring, Md.). Using a green filter, this instrument measured reflectance of color changes from white to black and was used in accordance with methods prescribed by The American Society For Testing And Materials (ASTM 1977). The upper limit of the reflectant scale was measured at 79 for an unexposed white sheet using the commercial Propper Once-A-Day test sheet and 8.5 for a completely exposed black sheet. Surface area of the incompletely exposed portion of test sheet was measured by calculating the area of the ellipse that best described the perimeter of the incompletely exposed area.

The tests revealed that in the range of reaction of primary interest, the effects of the two common flaws on the test sheets were substantially the same for the test pack of the present invention and a test pack prepared in accordance with the conventional Bowie and Dick protocol.

Referring now to FIG. 5, a conventional multilayer test pack for use in the United States contains a total of 18 layers (17 sheets) intermediate the test sheet and each bundle end surface, and has overall dimensions of about 5×5×⅞ inches (length X width X height). Because the bundles of the multilayer test packs are typically symmetrical about the test sheet, a schematic representation thereof shows only the portion of the bundle to one side of the test sheet, the test sheet theoretically being to the left of the schematic representation and the bundle end surface being to the right of the schematic representation. The conventional bundle is schematically represented in FIG. 5A where The number in a square represents the number of low porosity 214 basis paper sheets;

The number in a circle represents the number of higher porosity 178 basis paper sheets;

L represents a low porosity 214 basis paper having a non-porous layer on the surface thereof facing the bundle end surface;

Reverse L (i.e., ( ) indicates a low porosity 214 basis paper having a non-porous layer on the surface thereof facing the test sheet; and Combined L and reverse L (i.e., ⊥, an inverted "T") indicates a low porosity 214 basis paper having a non-porous layer on each of the opposed surfaces thereof.

The preferred U.S. multilayer test pack according to the present invention, having the bundle schematically represented in FIG. 5B, presents substantially the same challenge as the FIG. 5A conventional multilayer test pack, but utilizes only a total of 13 layers (11 sheets) between the test sheet and each bundle end surface and has overall dimensions of about 4×4×9/16 inches. It will be appreciated that the U.S. equivalent bundle according to the present invention is therefore more compact: an inch less in length, an inch less in width, and over ¼ inch less in height than the conventional test pack bundle for U.S. use.

The test pack according to the present invention having the bundle schematically represented in FIG. 5C is almost as good as the FIG. 5B test pack, but is not quite as good and requires one additional layer (i.e., 14 layers or 12 sheets). The test pack according to the present invention having the bundle schematically represented in FIG. 5D is only slightly less satisfactory than the FIG. 5C test pack having the same number of layers.

It will be appreciated that in the FIG. 5A bundle there is but a single non-porous layer 40 between the test sheet 30 and a bundle end surface 20, 22, in the FIG. 5B bundle there is a pair of non-porous layers 40 separated only by a porous layer 32, in the FIG. 5C bundle there is a pair of non-porous layers 40 separated by not only a porous layer 32 but also whatever space exists between two sheets, and in the FIG. 5D bundle there is a pair of non-porous layers 40 separated by two porous layers 32 and whatever empty space exists between two sheets.

Referring now to FIG. 6, a conventional multilayer test pack for use in Europe (where a more stringent challenge is used than in the U.S.) has a total of 22 layers (20 sheets) intermediate the test sheet and each bundle end surface, and has overall dimensions of about 5×4×1 inches. The bundle is schematically represented in FIG. 6A.

The European multilayer test pack according to the Present invention having the bundle schematically represented in FIG. 6B presents substantially the same challenge as the FIG. 6A bundle, but utilizes only a total of 18 layers (15 sheets) between the test sheet and each bundle end surface and had overall dimensions of about 4×4×¾ inches. It will be appreciated that the European equivalent bundle according to the present invention is more compact: an inch less in length and a ¼ inch less in height than the conventional European multilayer test pack bundle.

The multilayer test pack according to the present invention having the bundle schematically represented in FIG. 6C is substantially similar, although not quite as good, as the FIG. 6B test pack and requires an additional layer (and sheet).

It will be appreciated that in the conventional European test pack of FIG. 6A there is no "pair of non-porous layers", as that term is defined herein, as the two non-porous layers are separated by 10 porous layers (rather than the specified maximum of 2 porous layers between the non-porous layers of the pair of non-porous layers 40). The test pack according to the present invention having a FIG. 6B bundle includes a sheet comprised of a porous sheet having a non-porous layer on either side thereof (similar to the FIG. 5B bundle), and the test pack according to the present invention having a FIG. 6C bundle has the two non-porous layers of pairs separated by a porous sheet and whatever air space exists between two sheets (similar to the FIG. 5C bundle). It will be appreciated that the outermost non-porous layer 40 of the FIG. 6B and 6C bundles is too far spaced from the nearest non-porous layer 40 (3 porous layers 32 away) to be considered part of a pair of non-porous layers 40, but the innermost non-porous layer 40 (separated from the test sheet 30 by only a single porous layer 32) is separated from the next outer non-porous layer 40 by only two porous layers 32 and thus qualifies as part of a pair of non-porous layers 40, thus making the "pair" into a "triplet". The triplet of non-porous layers 40 conforms to the rule that the adjacent non-porous layers 40 within a triplet are separated by at least one and not more than two porous layers 32 (the air spaces between sheets not being considered for the purposes of this rule).

The foregoing examples illustrate that, contrary to the conventional wisdom, a compact test pack may be formed with reduced dimensions (on 1 axis, and preferably 2 or 3 axes), while still maintaining substantially the same challenge, by using at least a pair of non-porous layers in close proximity.

To summarize, the present invention provides a small, inexpensive and disposable test pack for use in prevacuum steam sterilizers to determine whether the sterilizer is functioning in accordance with the proper standards by simulating air evacuation and steam penetration conditions with the conventional test pack described in the Bowie and Dick protocol so as to define an appropriate challenge for a residual air test in a prevacuum sterilizer. The test pack provides a repeatable and consistent standard for testing the working order of the sterilizer from day to day and from sterilizer to sterilizer, and it requires neither assembly by hospital personnel nor the use of hospital linen or laundry for its initial use. The test pack according to the present invention utilizes fewer layers than other comparable multilayer test packs and is thus more compact than a conventional multilayer test pack offering a similar challenge in at least one and preferably two or even three dimensions.

Now that the preferred embodiments of the present invention have been shown and described in detail, various modifications and improvements thereon will become readily apparent to those skilled in the art. Accordingly, the appended claims are to be construed broadly and in a manner consistent with the spirit and scope of the invention described herein.

I claim:

1. A compact prevacuum steam sterilization test pack for testing the efficiency of a vacuum system of a steam sterilizer apparatus to create a vacuum, comprising
   (a) a bundle having a pair of end surfaces including a top surface and a bottom surface, a plurality of layers therebetween in flow communication generally parallel to each other and to said top and bottom surfaces, and an edge formed by said plurality of layers and extending between aid top surface and said bottom surface generally transverse to said layers, said bundle including:
      (i) a porous test sheet with a steam sensitive indicator ink printed thereon positioned between layers of said bundle to indicate the efficiency of the vacuum system of a sterilizer;
      (ii) a plurality of selectively porous layers within said bundle above and below said test sheet; and
      (iii) at least one pair of non-porous gas-impermeable layers disposed intermediate said test sheet and one of said end surfaces and spaced from both said test sheet and said one end surface by at least one of said porous layers, said non-porous layers of said pair of non-porous layers being laminated to opposed surfaces of a single one of said porous layers; the number, the position and spacing apart of said non-porous layers depending upon the level of efficiency desired in order to pass the test; and
   (B) a porous overwrap folded about said bundle to maintain the integrity thereof.

2. The pack of claim 1 wherein said bundle has layers of about four inches by about four inches in plan cross-section.

3. The pack of claim 1 wherein said pair of non-porous layers is closer to said test sheet than to said one end surface.

4. The pack of claim 1 wherein said pair of non-porous layers is spaced from said one end surface by a greater number of porous layers than it is from said test sheet.

5. The pack of claim 1 wherein said bundle includes a plurality of said pairs of said non-porous layers.

6. The pack of claim 5 wherein at least one of said pairs of non-porous layers are disposed to each side of said test sheet.

7. The pack of claim 6 wherein at least a triplet of said non-porous layers are disposed to each side of said test sheet, with each non-porous layer of said triplet being spaced apart from an adjacent non-porous layer of said triplet by at least one and no more than two of said porous layers.

8. The pack of claim 1 wherein each of said non-porous layers is thinner than one of said porous layers.

9. The pack of claim 1 wherein said non-porous layers are gas-impermeable plastic.

10. The pack of claim 1 wherein said pair of non-porous layers are composed, configured and dimensioned to restrict the escape of gas from said bundle therethrough when steam enters said bundle during operation of a sterilizer and to establish the amount of exposure of said indicator ink on said test sheet to steam as an indication of the efficiency of the vacuum system of the sterilizer.

11. A disposable compact prevacuum steam sterilization test pack for testing the efficiency of the vacuum system of a steam sterilizer apparatus to create a vacuum comprising (A) a bundle having a pair of end surfaces including a top surface and a bottom surface, a plurality of layers therebetween in flow communication generally parallel to each other and to said top and bottom surfaces, and an edge formed by said plurality of layers and extending between said top surface and said bottom surface generally transverse to said layers, said bundle including:

(i) a porous test sheet with a steam sensitive indicator ink printed thereon positioned between 14 said layers of said bundle to indicate the efficiency of the vacuum system of a sterilizer;

(ii) a plurality of selectively porous layers within said bundle above and below said test sheet; and (iii) at least one pair of non-porous gas-impermeable layers disposed intermediate said test sheet and each one of said end surfaces and spaced from both said test sheet and said one end surface by at least one of said porous layers, said non-porous layers in each said pair of non-porous layers being laminated to opposed surfaces of a single one of said porous layers, said pair of non-porous layers being closer to said test sheet than to said one end surface, and said non-porous layers of said pair of non-porous layers being spaced from said one end surface by a greater number of porous layers than it is from said test sheet; the number, the position and spacing apart of said non-porous layers depending upon the level of efficiency desired in order to pass the test; and (B) a porous overwrap folded about said bundle to maintain the integrity thereof;

whereby said pairs of non-porous layers are composed, configured and dimensioned to restrict the escape of gas from said bundle therethrough when steam enters said bundle during operation of a sterilizer and establish the amount of exposure of said indicator ink on said test sheet to steam as an indication of the efficiency of the vacuum system of the sterilizer.

12. The pack of claim 11 wherein at least a triplet of said non-porous layers are disposed to each side of said test sheet, with each non-porous layer of said triplet being spaced apart from an adjacent non-porous layer of said triplet by at least one and no more than two of said porous layers.

* * * * *